US006903098B1

(12) United States Patent
Lubisch et al.

(10) Patent No.: US 6,903,098 B1
(45) Date of Patent: Jun. 7, 2005

(54) USE OF PHTHALAZINE DERIVATIVES

(75) Inventors: Wilfried Lubisch, Heidelberg (DE); Jens Sadowski, Limburgerhof (DE); Michael Kock, Schifferstadt (DE); Thomas Höger, Edingen-Neckarhausen (DE)

(73) Assignee: Abbott GmbH & Co., Wiesbaden (DE)

(*) Notice: Subject to any disclaimer, the term of this patent is extended or adjusted under 35 U.S.C. 154(b) by 0 days.

(21) Appl. No.: 09/959,404

(22) PCT Filed: May 3, 2000

(86) PCT No.: PCT/EP00/03967

§ 371 (c)(1), (2), (4) Date: Jul. 2, 2002

(87) PCT Pub. No.: WO00/67734

PCT Pub. Date: Nov. 16, 2000

(30) Foreign Application Priority Data

Mar. 11, 1999 (DE) .......................... 199 21 567

(51) Int. Cl.⁷ ..................... A61K 31/495; C07D 237/30
(52) U.S. Cl. ...................... 514/248; 544/237
(58) Field of Search .......................... 544/237; 514/248

(56) References Cited

U.S. PATENT DOCUMENTS 4,939,140 A * 7/1990 Larson et al. ............... 514/222

FOREIGN PATENT DOCUMENTS

| EP | 0 722 936 A1 | 2/1996 |
| GB | 2 112 389 A | 7/1983 |
| WO | WO 98/45292 A1 | 10/1998 |
| WO | WO 99/11649 A2 | 3/1999 |
| WO | WO 99/64572 A3 | 12/1999 |
| WO | WO 00/05218 A1 | 2/2000 |
| WO | WO 00/05219 A1 | 2/2000 |

OTHER PUBLICATIONS

J. zhang, Guilford Pharmaceuticals Inc. PARP inhibition: a novel approach to treat ischaemia/reperfusion and inflammation–related injuries, Emerging Drugs: The prospect for improved Medicines Annual Executive Briefing 1999.*
Stefan Peukert et al., New inhibitors of poly(ADP–ribose-)polymerase (PARP); Expert Opinion Ther. Patents (2004) 14(11): 1531–1551.*
K. Ikai et al., J. Histochem. Cytochem. 1983, 31, 1261–1264.
M.S. Satoh et al., Nature 1992, 356, 356–358.
S. Shall, Adv. Radiat. Biol. 1984, 11, 1–69.
C. Thiemermann et al., Proc. Natl. Acad. Sci. USA 1997, 94, 679–683.
G. Chen et al., Cancer Chemo. Pharmacol, 1988, 22, 303.
D. Weltin et al., Int. J. Immunopharmacol 1995, 17, 265–271.
H. Kroger et al., Inflammation 1996, 20, 203–215.
W. Ehrlich et al., Rheumatol. Int. 1995, 15, 171–172.
C, Szabo et al., Proc. Natl. Acad. Sci. USA 1998, 95, 3867–3872.
C. Cuzzocrea et al., Eur. J. Pharmacol. 1988, 342, 67–76.
C. Cuzzocrea et al., Br. J. Pharmacol. 1997, 121, 1065–1074.
V. Burkart et al., Nature Med. 1999, 5, 314–319.
Puodzhyunas et al., Pharm. Chem. J. 1973, 7, 566.
Mazkanowa et al., Zh. Obsheh, Khim, 1958, 28, 2822.
F. K. Mohamed et al., Ind. J. Chem. B. 1994, 33, 769.
J. Singh et al., Ind. J. Chem. B. 1983, 22, 1083.

* cited by examiner

*Primary Examiner*—Johann Richter
*Assistant Examiner*—Ebenezer Sackey
(74) *Attorney, Agent, or Firm*—Wood, Phillips, Katz, Clark & Mortimer

(57) ABSTRACT

The present invention relates to the use of phthalazine derivatives as inhibitors of the enzyme poly(ADP-ribose) polymerase or PARP (EC 2.4.2.30), to the use as inhibitors of PARP-homologous enzymes and, in particular, these phthalazine derivatives also show a selective inhibition of PARP-homologous enzymes.

19 Claims, No Drawings

USE OF PHTHALAZINE DERIVATIVES

The present invention relates to the use of phthalazine derivatives as inhibitors of the enzyme poly(ADP-ribose) polymerase or PARP (EC 2.4.2.30), to the use as inhibitors of PARP-homologous enzymes and, in particular, these phthalazine derivatives also show a selective inhibition of PARP-homologous enzymes.

Poly(ADP-ribose) polymerase (PARP) or, as it is also called, poly(ADP-ribose) synthase (PARS) is a regulatory enzyme found in cell nuclei (K. Ikai et al., *J. Histochem. Cytochem.* 1983, 31, 1261–1264). It is assumed that PARP is involved in the repair of DNA breaks (M. S. Satoh et al., *Nature* 1992, 356, 356–358). Damage or breaks in DNA strands activate the enzyme PARP which, when it is activated, catalyzes the transfer of ADP-ribose from NAD (S. Shaw, *Adv. Radiat. Biol.*, 1984, 11, 1–69). During this, nicotinamide is released from NAD. Nicotinamide is converted back into NAD by other enzymes with consumption of the energy carrier ATP. Overactivation of PARP would accordingly result in a nonphysiologically large consumption of ATP, and this leads in the extreme case to cell damage and cell death.

It is known that free radicals such as superoxide anion, NO and hydrogen peroxide may lead to DNA damage in cells and thus activate PARP. The formation of large amounts of free radicals is observed in a number of pathophysiological states, and it is assumed that this accumulation of free radicals leads or contributes to the observed cell or organ damage. This includes, for example, ischemic states of organs as in stroke, myocardial infarct (C. Thiemermann et al., *Proc. Natl. Acad. Sci. USA,* 1997, 94, 679–683) or ischemia of the kidneys, but also reperfusion damage as occurs, for example, after lysis of myocardial infarct (see above: C. Thiemermann et al.). Inhibition of the enzyme PARP might accordingly be a means of at least partly preventing or moderating this damage. PARP inhibitors might thus represent a novel therapeutic principle for treating a number of diseases.

The enzyme PARP influences the repair of DNA damage and might thus also play a part in the therapy of cancers, since a greater action potential on tumor tissue was observed (G. Chen et al. *Cancer Chemo. Pharmacol.* 1988, 22, 303) in combination with substances with cytostatic activity.

In addition, it has been found that PARP inhibitors may show an immunosuppressant effect (D. Weltin et al. *Int. J. Immunopharmacol.* 1995, 17, 265–271).

It has likewise been discovered that PARP is involved in immunological disorders or diseases in which the immune system plays an important part, such as, for example, rheumatoid arthritis and septic shock, and that PARP inhibitors may show a beneficial effect on the course of the disease (H. Kröger et al. *Inflammation* 1996, 20, 203–215; W. Ehrlich et al. *Rheumatol. Int.* 1995, 15, 171–172; C. Szabo et al., *Proc. Natl. Acad. Sci. USA* 1998, 95, 3867–3872; S. Cuzzocrea et al. *Eur. J. Pharmacol.* 1998, 342, 67–76).

In addition, the PARP inhibitor 3-aminobenzamide showed protective effects in a model of circulatory failure (S. Cuzzocrea et al., *Br. J. Pharmacol.* 1997, 121, 1065–1074).

There is likewise experimental evidence that inhibitors of the 20 enzyme PARP might be of benefit as agents for treating diabetes mellitus (V. Burkart et al. *Nature Med.* 1999, 5, 314–319).

Phthalazines and derivatives thereof represent a widely used class of substances. 2H-Phthalazin-1-ones additionally having substituents in position 4 have, however, not been extensively described to date. Thus, methyleneamides, methyleneureas and methyleneimides have been described in Puodzhyunas et al. Pharm. Chem. J. 1973, 7, 566; W. Mazkanowa et al., Zh. Obshch. Khim. 1958, 28, 2822 und in F. K. Mohamed et al., Ind. J. Chem. B, 1994, 33, 769. Cyclic amines and alkylamines where the amino group may be both a cyclic and an aliphatic amine have been described in J. Singh et al., Ind. J. Chem. B, 1983, 22, 1083, Y. Egushi et al., Chem Pharm. Bull. 1991, 9, 1846 and in Iyo Kizai Kenkyusho Hokoku, 1998, 12, 41 (CA 91, 91579), although the compounds were investigated for antiatherosclerotic effects, for inhibition of blood platelet aggregation or for lowering of blood pressure. WO 99/11649 mentions phthalazinones which have phenylpiperazinylmethyl radicals in position 4 and which were described as inhibitors of the enzyme PARP.

2H-Phthalazinones with phenoxymethyl derivatives in position 4 were prepared in A. M. Bernard et al., Synthesis 1998, 317.

The present invention describes novel phthalazine derivatives of the general formula I which are, surprisingly, PARP inhibitors.

It has also been found, surprisingly, that these compounds of the general formula I also inhibit PARP-homologous enzymes. In addition, these compounds surprisingly show a selective inhibition of the PARP-homologous enzymes, i.e. the compounds inhibit the homologous enzymes more strongly than the enzyme PARP itself.

The phthalazines according to the invention preferably show an inhibitory effect which is 5 times stronger on PARP homologs (PARP 2) than on the known PARP (PARP 1). PARP homologs mean, in particular, the homolog PARP-2 as claimed in WO 99/64572 (human PARP2). This can be isolated advantageously from human brain, heart, skeletal muscle, kidney and liver. The expression of human PARP2 is distinctly less in other tissues and organs.

The human PARP2 which can be isolated from human brain, and its functional equivalents, in particular are preferred agents for developing inhibitors for stroke. This is because it can be assumed that the development of active substances based on PARP2 as indicator will make it possible to develop inhibitors which are optimized for use on human brain. However, it cannot be precluded that inhibitors developed on the basis of PARP2 can also be employed for the therapy of PARP-mediated pathological states in other organs. Based on the tissue distribution of the proteins according to the invention, indications of particular interest are those involving ischemic states of appropriate organs (ischemia of the brain (stroke), of the heart (myocardial infarction), damage during or after infarct lysis (for example with TPA, reteplase or mechanically with laser or Rotablator) and microinfarcts during and after heart valve replacement, aneurysm resections and heart transplants, of the kidney (acute kidney failure, acute renal insufficiency or damage during and after a kidney transplant), damage to the liver or the skeletal muscle). Also conceivable are the treatment and prophylaxis of neurodegenerative disorders occurring after ischemia, trauma (craniocerebral trauma), massive bleeding, subarachnoid hemorrhages and stroke, and of neurodegenerative disorders such as multi-infarct dementia, Alzheimer's disease, Huntington's disease and epilepsies, especially generalized epileptic seizures such as, for example, petit mal, and tonoclonic seizures and partial epileptic seizures such as temporal lobe, and complex partial seizures. Said proteins may also be relevant in treatment for revascularization of critically narrowed coronary arteries and critically narrowed peripheral arteries, for example leg arteries. Said proteins may additionally play a part in the chemotherapy of tumors and in the prevention of metastases, and in the treatment of inflammations and rheumatic disorders, for example of rheumatoid arthritis. Further pathological states of these and other organs are conceivable.

PARP2 resembles PARP1 in being activated by damaged DNA, although the mechanism is presumably different. Importance in DNA repair is conceivable. Inhibition of the PARPs according to the invention would also be of benefit in indications such as cancer (for example in the radiosensitization of tumor patients).

The specific assay systems described above for binding partners of PARP1 and PARP2 were used to develop active and selective inhibitors of the proteins according to the invention.

Inhibitors provided according to the invention have a very pronounced inhibitory activity on PARP2. The $K_i$ values may in this case be less than about 1000 nM, such as, for example, less than about 700 nM, less than about 100 nM and less than about 30 nM, such as, for example, about 1 to 20 nM.

Inhibitors which are preferred according to the invention have a surprisingly pronounced selectivity for PARP2. The $K_i$(PARP1): $K_i$(PARP2) ratio for inhibitors according to the invention is accordingly greater than 5, for example. Another group of inhibitors was developed to inhibit PARP1 and PARP2 simultaneously.

For expression in a suitable host organism, the recombinant nucleic acid construct or gene construct is advantageously inserted into a host-specific vector which makes optimal expression of the genes possible in the host. Vectors are well known to the skilled worker and can be found, for example, in "Cloning Vectors" (Pouwels P. H. et al., editors, Elsevier, Amsterdam-N.Y.-Oxford, 1985). Vectors mean apart from plasmids also all other vectors known to the skilled worker, such as, for example, phages, viruses such as SV40, CMV, baculovirus and adenovirus, transposons, IS elements, phasmids, cosmids, and linear or circular DNA. These vectors can undergo autonomous replication in the host organism or chromosomal replication.

Expression of the Constructs

It is advantageous for the recombinant constructs according to the invention described above to be introduced into and expressed in a suitable host system. In this connection, the cloning and transfection methods known and familiar to the skilled worker are preferably used for bringing about expression of said nucleic acids in the particular expression system. Suitable systems are described, for example, in Current Protocols in Molecular Biology, F. Ausubel et al., editors, Wiley Interscience, New York 1997.

Suitable host organisms are in principle all organisms allowing expression of the nucleic acids according to the invention, their allelic variants, their functional equivalents or derivatives or of the recombinant nucleic acid construct. Host organisms mean, for example, bacteria, fungi, yeasts, plant or animal cells. Preferred organisms are bacteria such as those of the genera *Escherichia*, such as, for example, *Escherichia coli, Streptomyces, Bacillus* or *Pseudomonas*, eukaryotic microorganisms such as *Saccharomyces cerevisiae, Aspergillus*, higher eukaryotic cells from animals or plants, for example Sf9 or CHO cells.

If required, expression of the gene product can also take place in transgenic organisms such as transgenic animals such as, in particular, mice, sheep or transgenic plants. The transgenic organisms may also be so-called knockout animals or plants in which the corresponding endogenous gene has been switched off, such as, for example, by mutation or partial or complete deletion.

Combination of the host organisms and the vectors appropriate for the organisms, such as plasmids, viruses or phages, such as, for example, plasmids with the RNA-polymerase/promoter system, phages λ, μ or other temperate phages or transposons and/or other advantageous regulatory sequences form an expression system. The term expression systems preferably means, for example, a combination of mammalian cells such as CHO cells, and vectors such as the pcDNA3neo vector, which are suitable for mammalian cells.

As described above, expression of the gene product can also take place advantageously in transgenic animals, for example mice, sheep or transgenic plants. It is likewise possible to program cell-free translation systems with the RNA derived from the nucleic acid.

Production of Antibodies:

The production of anti-PARP2 antibodies takes place in a manner familiar to the skilled worker. Antibodies mean either polyclonal, monoclonal, human or humanized antibodies or fragments thereof, single chain antibodies or else synthetic antibodies, as well as antibody fragments such as Fv, Fab and F(ab')$_2$. Suitable production processes are described, for example, in Campbell, A. M., Monoclonal Antibody Technology, (1987) Elsevier Verlag, Amsterdam, N.Y., Oxford and in Breitling, F. and Dübel, S., Rekombinante Antikörper (1997), Spektrum Akademischer Verlag, Heidelberg.

EXAMPLE A

Isolation of the PARP2 cDNA

The present cDNA sequences were found for the first time on sequence analysis of cDNA clones in a human brain cDNA library (Human Brain 5' Stretch Plus cDNA Library, # HL3002a, from Clontech). The sequence of this clone is described in SEQ ID NO:1.

EXAMPLE B

Production of the Enzymes

For comparison, human PARP1 was expressed recombinantly in the baculovirus system in the manner familiar to the skilled worker, and was partially purified as described (Shah et al., Analytical Biochemistry 1995, 227, 1–13). Bovine PARP1 in a purity of 30–50% (c=0.22 mg/ml, spec. activity 170 nmol of ADP-ribose/min/mg total protein at 25° C.) was purchased from BIOMOL (order No. SE-165). Human PARP2 were expressed recombinantly in the baculovirus system (Bac-to-Bac System, BRL LifeScience). For this purpose, the corresponding cDNAs were cloned into the pFASTBAC-1 vector. After production of recombinant baculovirus DNA by recombination in *E. coli*, insect cells (Sf9 or high five) were transfected with the corresponding recombinant baculovirus DNAs. Expression of the corresponding proteins was verified by Western blot analysis. Viral strains were amplified in the manner familiar to the skilled worker. Larger amounts of recombinant proteins were infected by infection of 500 ml of insect cell culture ($2 \times 10^6$ cells/ml) with viruses in an MOI (multiplicity of infection; ratio of viruses to cells) of 5–10 and incubated for 3 to 4 days. The insect cells were then pelleted by centrifugation and the proteins were purified from the pellet.

The purification took place by classical methods of protein purification which are familiar to the skilled worker, with detection of the enzymes using appropriate specific antibodies. In some cases, the proteins were also affinity-purified on a 3-aminobenzamide affinity column as described (Burtscher et al., Anal Biochem 1986, 152:285–290). The purity was >90%.

EXAMPLE C

Assay Systems for Determining the Activity of PARP2 and the Inhibitory Effect of Effectors on PARP1 and PARP2 a) Production of Antibodies Against poly(ADP-ribose)

Poly(ADP-ribose) can be used as antigen for generating anti-poly(ADP-ribose) antibodies. The production of anti-poly(ADP-ribose) antibodies is described in the literature (Kanai Y et al. (1974) Biochem Biophys Res Comm 59:1, 300–306; Kawamaitsu H et al. (1984) Biochemistry 23, 3771–3777; Kanai Y et al. (1978) Immunology 34, 501–508).

The following were used, inter alia: anti-poly(ADP-ribose) antibodies (polyclonal antiserum, rabbit), BIOMOL; order No. SA-276. Anti-poly(ADP-ribose) antibodies (monoclonal, mouse; clone 10H; hybridoma supernatant, affinity-purified).

The antisera or monoclonal antibodies obtained from hybridoma culture supernatant were purified by protein A affinity chromatography in the manner familiar to the skilled worker.

b) ELISA—Assay
Materials:
ELISA Color Reagent: TMB Mix SIGMA T-8540

A 96-well microtiter plate (FALCON Micro-Test IIIa Flexible Assay Plate, # 3912) was coated with histones (SIGMA, H-7755). Histones were for this purpose dissolved in carbonate buffer (0.05M $NaHCO_3$; pH 9.4) in a concentration of 50 µg/ml. The individual wells of the microtiter plate were each incubated with 150 µl of this histone solution at room temperature for at least 2 hours or at 4° C. overnight. The wells were then blocked by adding 150 µl of a 1% strength BSA solution (SIGMA, A-7888) in carbonate buffer at room temperature for 2 hours. This is followed by three washing steps with washing buffer (0.05% Tween10 in 1×PBS; PBS (Phosphate buffered saline; Gibco, order No. 10010): 0.21 g/l $KH_2PO_4$, 9 g/l NaCl, 0,726 g/l $Na_2HPO_4.7H_2O$, pH 7.4). Wash steps were all carried out in a microtiter plate washer ("Columbus" microtiter plate washer, SLT-Labinstruments, Austria).

Required for the enzyme reaction were an enzyme reaction solution and a substrate solution, in each case as a premix. The absolute amount of these solutions depended on the intended number of assay wells.

Composition of the enzyme reaction solution per well:
4 µl of PARP reaction buffer (1M Tris-HCl pH 8.0, 100 mM $MgCl_2$, 10 mM DTT)
20 ng of PARP1 (human or bovine) or 8 ng of PARP2 (human)
4 µl of activated DNA (1 mg/ml; SIGMA, D-4522)
ad 40 µl $H_2O$ Composition of the substrate solution per well:
5 µl of PARP reaction buffer (10×)
0.8 µl of NAD solution (10 mM, SIGMA N-1511)
44 µl of $H_2O$ Inhibitors were dissolved in 1× PARP reaction buffer. DMSO, which was occasionally used to dissolve inhibitors in higher concentrations, was no problem up to a final concentration of 2%. For the enzyme reaction, 40 µl of the enzyme reaction solution were introduced into each well and incubated with 10 µl of the inhibitor solution for 10 minutes. The enzyme reaction was then started by adding 50 µl of substrate solution per well. The reaction was carried out at room temperature for 30 minutes and then stopped by washing three times with washing buffer.

The primary antibodies employed were specific anti-poly (ADP-ribose) antibodies in a dilution of 1:5000. Dilution took place in antibody buffer (1% BSA in PBS; 0.05% Tween20). The incubation time for the primary antibody was one hour at room temperature. After subsequently washing three times with washing buffer, incubation was carried out with the secondary antibody (anti-mouse IgG, Fab fragments, peroxidase-coupled, Boehringer Mannheim, order No. 1500.686; anti-rabbit IgG, peroxidase-coupled, SIGMA, order No. A-6154) in a 1:10000 dilution in antibody buffer at room temperature for one hour. Washing three times with washing buffer was followed by the color reaction using 100 µl of color reagent (TMB mix, SIGMA) per well at room temperature for about 15 min. The color reaction was stopped by adding 100 µl of 2M $H_2SO_4$. This was followed by immediate measurement in an ELISA plate reader (EAR340AT "Easy Reader", SLT-Labinstruments, Austria) (450 nm versus 620 nm). The principle of measurement is depicted diagrammatically in FIG. 6.

Various concentrations were used to construct a dose-effect plot to determine the $K_i$ of an inhibitor. Values are obtained in triplicate for a particular inhibitor concentration. Arithmetic means are determined using Microsoft® Excel. The $IC_{50}$ is determined using the Microcal® Origin Software (Vers. 5.0) ("Sigmoidal Fit"). Conversion of the $IC_{50}$ values calculated in this way to $K_i$ took place using "calibration inhibitors". The "calibration inhibitors" were also measured in each analysis. The $K_i$ values of the "calibration inhibitors" were determined in the same assay system by analysis of the Dixon diagramm in the manner familiar to the skilled worker.

c) HTRF (Homogenous Time-Resolved Fluorescence) Assay

In the HTRF PARP assay according to the invention, histones, as target proteins for modification by PARP, are labeled indirectly with an XL665 fluorophore. The antibody is labeled directly with a europium cryptate. If the XL665 fluorophore is in the direct vicinity in space, which is ensured by binding to the poly(ADP-ribose) on the histone, then an energy transfer is possible. The emission at 665 nm is thus directly proportional to the amount of bound antibody, which in turn is equivalent to the amount of poly(ADP-ribose). The measured signal thus corresponds to the PARP activity. The principle of measurement is depicted diagrammatically in FIG. 7. The materials used are identical to those used in the ELISA (see above) unless expressly stated.

Histones were dissolved in a concentration of 3 mg/ml in Hepes buffer (50 mM, pH=7.5). Biotinylation took place with sulfo-NHS-LC-biotin (Pierce, #21335T). A molar ratio of 4 biotin per histone was used. The incubation time was 90 minutes (RT). The biotinylated histones were then purified on a G25 SF HR10/10 column (Pharmacia, 17-0591-01) in Hepes buffer (50 mM, pH=7.0) in order to remove excess biotinylation reagent. The anti-poly(ADP-ribose) antibody was labeled with europium cryptate using bifunctional coupling reagents (Lopez, E. et al., Clin. Chem. 39(2), 196–201 (1993); U.S. Pat. No. 5,534,622). Purification took place on a G25SF HR10/30 column. A molar ratio of 3.1 cryptates per antibody was achieved. The yield was 25%. The conjugates were stored at −80° C. in the presence of 0.1% BSA in phosphate buffer (0.1 M, pH=7).

For the enzyme reaction, the following were pipetted into each well:

10 μl of PARP solution in PARP HTRF reaction buffer (50 mM Tris-HCl pH 8.0, 10 mM MgCl$_2$, 1 mM DTT) with 20 ng of PARP1 (human or bovine) or 8 ng of PARP2 (human)

10 μl of activated DNA in PARP HTRF reaction buffer (50 μg/ml)

10 μl of biotinylated histones in PARP HTRF reaction buffer (1.25 μM)

10 μl of inhibitor in PARP HTRF reaction buffer

These reagents were preincubated for 2 minutes before starting the reaction by adding 10 μl of NAD solution in PARP HTRF reaction buffer (400 μM/ml). The reaction time was 30 minutes at room temperature.

The reaction was then stopped by adding

10 μl of PARP inhibitor (25 μM, K$_i$=10 nM) in "Revelation" buffer (100 mM Tris-HCl pH 7.2, 0.2M KF, 0.05% BSA)

The following were then added:

10 μl of EDTA solution (SIGMA, E-7889, 0.5M in H$_2$O)

100 μl of Sa-XL665 (Packard Instruments) in "Revelation" buffer (15–31.25 nM)

50 μl of anti-PARP cryptate in "Revelation" buffer (1.6–3.3 nM).

Measurement was then possible after 30 minutes (up to 4 hours). The measurement took place in a "Discovery HTRF Microplate Analyzer" (Packard Instruments). The K$_i$ values were calculated as described for the ELISA.

The present invention relates to the use of substituted phthalazines of the general formula I

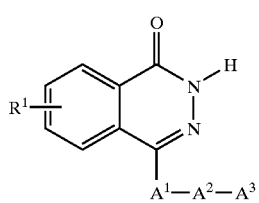

(I)

in which

R$^1$ is hydrogen, chlorine, fluorine, bromine, iodine, branched and unbranched C$_1$–C$_6$-alkyl, OH, nitro, CF$_3$, CN, NR$^{11}$R$^{12}$, NH—CO—R$^{13}$, O—C$_1$–C$_4$-alkyl, where R$^{11}$ and R$^{12}$ are, independently of one another, hydrogen or C$_1$–C$_4$-alkyl, and R$^{13}$ is hydrogen, C$_1$–C$_4$-alkyl, phenyl-C$_1$–C$_4$-alkyl or phenyl, and A$^1$ is a straight-chain or branched C$_0$–C$_6$-alkyl radical and A$^2$ is NR$^2$, NR$^2$—C$_1$–C$_6$-alkyl, O and S and R$^2$ is hydrogen and C$_1$–C$_6$-alkyl and A$^3$ is an aromatic or heteroaromatic ring with, in each case, 5 or 6 ring atoms and up to 3 heteroatoms selected from N, O, S, such as, for example, phenyl, thiophene, pyridine, pyrimidine, naphthalene, indole, imidazole, which may also be substituted by R$^4$ and one or two R$^3$, where R$^3$ can be hydrogen, chlorine, fluorine, bromine, iodine, branched and unbranched C$_1$–C$_6$-alkyl, OH, nitro, CF$_3$, CN, NR$^{11}$R$^{12}$, SO$_2$NR$^{11}$R$^{12}$, SO$_2$—C$_1$–C$_4$-alkyl, S—C$_1$–C$_4$-alkyl, O-Ph, O—CF$_3$, NH—CO—R$^{13}$, O—C$_1$–C$_4$-alkyl, where R$^{11}$ and R$^{12}$ are, independently of one another, hydrogen or C$_1$–C$_4$-alkyl, and R$^{13}$ can be hydrogen, C$_1$–C$_4$-alkyl, phenyl-C$_1$–C$_4$-alkyl or phenyl, R$^4$ is hydrogen, (X)$_{0,1}$—C$_1$–C$_4$-alkyl-NR$^{41}$R$^{42}$, where X=O, S and NR$^{43}$ and R$^{41}$ and R$^{42}$ can be, independently of one another, hydrogen, C$_1$–C$_6$-alkyl, phenyl-C$_1$–C$_4$-alkyl and a 3 to 7-membered cyclic amine and R$^{43}$ can be hydrogen and C$_1$–C$_4$-alkyl, and their tautomeric forms, possible enantiomeric and diastereomeric forms, and their prodrugs.

The compounds of the formula I can be employed as racemates, as enantiomerically pure compounds or as diastereomers. If enantiomerically pure compounds are required, these can be obtained, for example, by carrying out a classical racemate resolution with the compounds of the formula I or their intermediates using a suitable optically active base or acid.

The invention also relates to compounds which are mesomers or tautomers of compounds of the formula I.

The invention further relates to the physiologically tolerated salts of the compounds I, which can be obtained by reacting compounds I with a suitable acid or base. Examples of suitable acids and bases are listed in Fortschritte der Arzneimittelforschung, 1966, Birkhäuser Verlag, Volume 10, pp. 224–285. These include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and tris.

Prodrugs mean compounds which are metabolized in vivo to compounds of the general formula I. Typical prodrugs are phosphates, carbamates of amino acids, esters and others.

The phthalazine derivatives I according to the invention can be prepared in various ways, which have already been carried out in the literature.

The possible synthetic methods are described, for example, in Puodzhyunas et al. Pharm. Chem. J. 1973, 7, 566, W. Mazkanowa et al., Zh. Obshch. Khim. 1958, 28, 2822, F. K. Mohamed et al., Ind. J. Chem. B, 1994, 33, 769, J. Singh et al., Ind. J. Chem. B, 1983, 22, 1083, Y. Egushi et al., Chem Pharm. Bull. 1991, 9, 1846 und in Iyo Kizai Kenkyusho Hokoku, 1998, 12, 41 (CA 91, 91579) or have been cited therein. The compounds according to the invention can be prepared in analogy to the methods described therein.

The substituted phthalazines I comprised in the present invention are inhibitors of the enzyme poly(ADP-ribose) polymerase and show in particular selectivity for novel PARP-homologous enzymes.

The inhibitory effect of the substituted phthalazine derivatives I was determined using an enzyme assay which has already been disclosed in the literature, with a K$_i$ being determined as a gage of the effect. The phthalazine derivatives I were measured in this way for an inhibitory effect on the enzyme poly(ADP-ribose) polymerase or PARP (EC 2.4.2.30).

4-(4-phenylpiperazin-1-yl)methyl-2H-phthalazin-1-one was described in WO 99/11649 as PARP inhibitor and is structurally related to the compounds according to the invention. This compound was investigated in the stated HTRF assay for the PARP 1 inhibitory effect. This compound showed only a weak effect (38% inhibition at 10 μM) however.

It has now been found, surprisingly, that the compounds according to the invention not only inhibit PARP enzymes too, but are distinctly more effective (see table).

| Example | PARP1 $K_i/\mu M$ |
| --- | --- |
| 1 | 0.62 |
| 4 | 0.19 |
| 11 | 1.80 |
| 16 | 0.78 |
| 17 | 0.74 |
| 18 | 0.69 |

The substituted phthalazine derivatives of the general formula I are inhibitors of poly(ADP-ribose) polymerase (PARP) or, as it is also called, poly(ADP-ribose) synthase (PARS) and can thus be used for the treatment and prophylaxis of diseases associated with an increased activity of these enzymes.

The compounds of the formula I can be employed to produce drugs for treating damage following ischemias and for the prophylaxis of expected ischemias in various organs. The present phthalazine derivatives of the general formula I can accordingly be used for the treatment and prophylaxis of neurodegenerative diseases occurring after ischemia, trauma (craniocerebral trauma), massive bleeding, subarachnoid hemorrhages and stroke, and of neurodegenerative diseases such as multi-infarct dementia, Alzheimer's disease, Huntington's disease and of epilepsies, in particular of generalized epileptic seizures such as, for example, petit mal and tonoclonic seizures and partial epileptic seizures such as temporal lobe, and complex partial seizures, and further for the treatment and prophylaxis of damage to the heart after cardiac ischemia and damage to the kidneys after renal ischemia, for example of acute renal insufficiency, of acute kidney failure, or of damage occurring during and after a kidney transplant. The compounds of the general formula I can further be used to treat acute myocardial infarction and damage occurring during and after medical lysis thereof (for example with TPA, reteplase, streptokinase or mechanically with a laser or Rotablator) and of microinfarcts during and after heart valve replacement, aneurysm resections and heart transplants. The present phthalazines I can likewise be used for treatment in cases of revascularization of critically narrowed coronary arteries, for example in PTCA and bypass operations, and critically narrowed peripheral arteries, for example leg arteries. In addition, the phthalazines I can be beneficial in the chemotherapy of tumors and metastasis thereof and can be used to treat inflammations and rheumatic disorders such as, for example, rheumatoid arthritis, and for the treatment of diabetes mellitus.

The pharmaceutical preparations according to the invention contain a therapeutically effective amount of the compounds I in addition to conventional pharmaceutical excipients.

For local external use, for example in dusting powders, ointments or sprays, the active substances can be present in the usual concentrations. The active substances are ordinarily present in an amount of 0.001 to 1% by weight, preferably 0.001 to 0.1% by weight.

On internal use, the preparations are administered in single doses. From 0.1 to 100 mg are given per kg of body weight in a single dose. The preparation may be administered in one or more doses each day, depending on the nature and severity of the disorders.

Appropriate for the required mode of administration, the pharmaceutical preparations according to the invention comprise conventional carriers and diluents, in addition to the active substance. For local external use, it is possible to use pharmaceutical excipients such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is also possible for antioxidants such as tocopherol and butylated hydroxyanisole, and butylated hydroxytoluene, flavor-improving additives, stabilizers, emulsifiers and lubricants to be present.

The substances present in the preparation in addition to the active substance, and the substances used in the production of the pharmaceutical preparations are toxicologically acceptable and compatible with the particular active substance. The pharmaceutical preparations are produced in a conventional way, for example by mixing the active substance with conventional carriers and diluents.

The pharmaceutical preparations can be administered in various ways, for example orally, parenterally such as intravenously by infusion, subcutaneously, intraperitoneally and topically. Thus, possible presentations are tablets, emulsions, infusion and injection solutions, pastes, ointments, gels, creams, lotions, dusting powders and sprays.

EXAMPLES

Example 1

4(N(4-Hydroxyphenyl)aminomethyl)-2H-phthalazin-1-one $^1$H-NMR ($D_6$-DMSO): $\delta$=4.4 (2H), 5.5 (1H), 6.55 (4H), 7.75–8.3 (4H), 8.5 (1H) and about 12.5 (1H) ppm.

Example 2

4(N(4-(N,N-Dimethylsulfamoyl)phenyl)aminomethyl)-2H-phthalazin-1-one $^1$H-NMR ($D_6$-DMSO): $\delta$=2.5 (6H), 4.7 (2H), 6.8 (2H), 7.2 (1H), 7.5 (2H), 7.75–8.3 (4H), and about 12.5 (1H) ppm.

Example 3

4(N(4-Chlorophenyl)aminomethyl)-2H-phthalazin-1-one $^1$H-NMR ($D_6$-DMSO): $\delta$=4.6 (2H), 6.4 (1H), 6.75 (2H), 7.1 (2H), 7.9–8.4 (4H), and about 12.5 (broad) ppm.

Example 4

4(N-Phenylaminomethyl)-2H-phthalazin-1-one $^1$H-NMR ($D_6$-DMSO): $\delta$=4.6 (2H), 6.3 (1H), 6.2 (1H), 6.8 (2H), 7.1 (2H), 7.9–8.5 (4H) and about 12.5 (broad) ppm.

Example 5

4(N(3-Trifluoromethylphenyl)aminomethyl)-2H-phthalazin-1-one $^1$H-NMR ($D_6$-DMSO): $\delta$=4.6 (2H), 6.7 (1H), 6.8 (1), 7.0 (2H), 7.3 (1H), 7.9–8.4 (4H) and about 12.5 (broad) ppm.

Example 6

4(N(2-Cyanophenyl)aminomethyl)-2H-phthalazin-1-one $^1$H-NMR ($D_6$-DMSO): $\delta$ 4.8 (2H), 6.7 (2H), 7.1 (1H), 7.5–7.8 (2H), 7.95 (1H), 8.1 (1H), 8.4 (2H) and 12.5 (1H) ppm.

Example 7

4(N(4-Methoxyphenyl)aminomethyl)-2H-phthalazin-1-one $^1$H-NMR (D$_6$-DMSO): δ=3.7 (3H), 4.5 (2H), 5.8 (1H), 6.7 (4H), 7.9–8.3 (4H) and about 12.5 (broad) ppm.

Example 8

4(N(2,4-Dichlorophenyl)aminomethyl-2H-phthalazin-1-one $^1$H-NMR (D$_6$-DMSO): δ 4.8 (2H), 6.3 (1H), 7.0 (1H), 7.2 (1H), 7.4 (1H), 7.9 (1H), 8.0 (1H), 8.3 (2H) and about 12.5 (broad) ppm.

Example 9

4(N(4-Nitrophenyl)aminomethyl)-2H-phthalazin-1-one $^1$H-NMR (D$_6$-DMSO): δ=4.8 (2H), 6.8 (2H), 7.8–8.4 (7H) and about 12.5 (broad) ppm.

Example 10

4-(N(3-Methylmercaptophenyl)aminomethyl)-2H-phthalazin-1-one $^1$H-NMR (D$_6$-DMSO): δ=2.4 (3H), 4.6 (2H), 6.3 (1H), 6.4–6.7 (3H), 7.0 (1H), 7.9–8.4 (4H) and about 12.5 (broad) ppm.

Example 11

4(N(2,4-Difluorophenyl)aminomethyl)-2H-phthalazin-1-one $^1$H-NMR (D$_6$-DMSO): δ=4.7 (2H), 6.0 (1H), 7.0 (2H), 7.1 (1H), 7.9 (1H), 8.0 (1H), 8.3 (2H) and about 12.5 (broad) ppm.

Example 12

4(N(4-Phenoxyphenyl)aminomethyl)-2H-phthalazin-1-one $^1$H-NMR (D$_6$-DMSO): δ=4.6 (2H), 6.2 (1H), 6.8 (2H), 6.9 (3H), 7.1 (1H), 7.4 (2H), 8.0–8.5 (4H) and about 12.5 (1H) ppm.

Example 13

4(N(4-Trifluoromethoxyphenyl)aminomethyl)-2H-phthalazin-1-one $^1$H-NMR (D$_6$-DMSO): δ 4.6 (2H), 6.5 (1H), 6.75 (2H), 7.1 (2H), 7.8–8.4 (4H) and about 12.5 (1H) ppm.

Example 14

4(N(4-Trifluoromethylphenyl)aminomethyl)-2H-phthalazin-1-one $^1$H-NMR (D$_6$-DMSO): δ=4.7 (2H), 6.8 (2H), 6.95 (1H), 7.4 (2H), 7.8–8.4 (4H) and 12.5 (broad) ppm.

Example 15

4(N-Methyl-N-phenylaminomethyl)-2H-phthalazin-1-one ×HCl $^1$H-NMR (D$_6$-DMSO): δ 2.7 (1.5H), 3.0 (1.5H), 3.8 (0.5H), 4.0 (0.5H), 4.5 (1H), 4.9 (1H), 6.5–8.3 (9H) and about 12.5 (broad) ppm.

Example 16

4 (S(4-Chlorophenyl)mercaptomethyl)-2H-phthalazin-1-one $^1$H-NMR (D$_6$-DMSO): δ=4.6 (2H), 7.4 (4H), 7.9–8.5 (4H) and about 12.5 (broad) ppm.

Example 17

4(S(1-Methylimidazol-2-yl)mercaptomethyl)-2H-phthalazin-1-one

Example 18

4(N(5-Methylmercapto-1,3,4-triazol-2-yl)aminomethyl)-2H-phthalazin-1-one $^1$H-NMR (D$_6$-DMSO): δ=2.4 (3H), 4.7 (2H), 7.1 (1H), 7.8–8.3 (4H) and about 12.5 (broad) ppm.

Example 19

4(S(2-Pyridyl)mercaptomethyl)-2H-phthalazin-1-one $^1$H-NMR (D$_6$-DMSO): δ=4.8 (2H), 7.2 (1H), 7.4 (1H), 7.7 (1H), 7.9 (1H), 8.0 (1H), 8.2 (1H), 8.5 (1H) and about 12.5 (1H) ppm.

What is claimed is:

1. A method of treating a patient having a disorder characterized by increased activity of poly (ADP-ribose) polymerase (PARP), wherein said disorder to be treated is selected from the group consisting of: neuronal damage, Parkinson's disease, Huntington's disease, damage due to ischemia, epilepsy, damage to the heart following cardiac ischemia, microinfarcts, revascularization of critically narrowed coronary arteries, acute myocardial infarction and damage during and after medical or mechanical lysis thereof, treatment of sepsis or septic shock and diabetes mellitus, said method comprising the step of: administering to a patient in need of such treatment an effective amount of a compound of the formula I

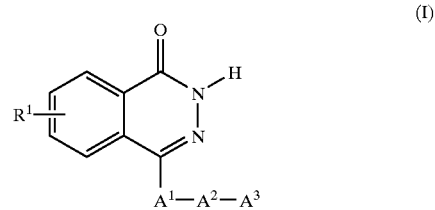

in which

R$^1$ is hydrogen, chlorine, fluorine, bromine, iodine, branched and unbranched C$_1$–C$_6$-alkyl, OH, nitro, CF$_3$, CN, NR$^{11}$R$^{12}$, NH—CO—R$^{13}$, O—C$_1$–C$_4$-alkyl, where R$^{11}$ and R$^{12}$ are, independently of one another, hydrogen or C$_1$–C$_4$-alkyl, and R$^{13}$ is hydrogen, C$_1$–C$_4$-alkyl, phenyl-C$_1$–C$_4$-alkyl or phenyl, and A$^1$ is a straight-chain or branched C$_0$–C$_6$-alkyl radical and A$^2$ is NR$^2$, NR$^2$—C$_1$–C$_6$-alkyl-, O or S and R$^2$ is hydrogen or C$_1$–C$_6$-alkyl and A$^3$ is an aromatic or heteroaromatic ring with, in each case, 5 or 6 ring atoms and up to 3 heteroatoms selected from N, O, and S, which may also be substituted by R$^4$ and one or two R$^3$, where R$^3$ can be hydrogen, chlorine, fluorine, bromine, iodine, branched and unbranched C$_1$–C$_6$- alkyl, OH, nitro, $CF_3$, CN, $NR^{11}R^{12}$, $SO_2NR^{11}R^{12}$, $SO_2$—$C_1$–$C_4$-alkyl, S—$C_1$–$C_4$-alkyl, O-Ph, O—$CF_3$, NH—CO—$R^{13}$, O—$C_1$–$C_4$-alkyl, where $R^{11}$ and $R^{12}$ are, independently of one another, hydrogen or $C_1$–$C_4$-alkyl, and $R^{13}$ can be hydrogen, $C_1$–$C_4$-alkyl, phenyl-$C_1$–$C_4$-alkyl or phenyl, $R^4$ is hydrogen, $(X)_{0,1}$—$C_1$–$C_4$-alkyl-$NR^{41}R^{42}$, where X=O, S and $NR^{43}$ or $R^{41}$ and $R^{42}$ can be independently of one another, hydrogen, $C_1$–$C_6$-alkyl, phenyl-$C_1$–$C_4$-alkyl or a 3 to 7-membered cyclic amine and $R^{43}$ can be hydrogen or $C_1$–$C_4$-alkyl, and its tautomeric forms, and its prodrugs.

2. The method as claimed in claim 1 wherein the compound is an inhibitor of PARP- or PARS-homologous enzymes.

3. The method as claimed in claim 1 wherein the compound is an inhibitor of PARP- or PARS-homologous enzymes, where the compound selectively inhibits these homologs by comparison with PARP or PARS itself.

4. The method as claimed in claim 1 wherein the compound is used for the treatment of neuronal damage.

5. The method as claimed in claim 4 wherein the neuronal damage is caused by ischemia, trauma or massive bleeding.

6. The method as claimed in claim 4 wherein the compound is used for the treatment of Parkinson's disease or Huntington's disease.

7. The method as claimed in claim 1 wherein the compound is used for the treatment or prophylaxis of damage due to ischemia.

8. The method as claimed in claim 1 wherein the compound is used for the treatment of epilepsies.

9. The method as claimed in claim 1 wherein the compound is used for the treatment of damage to the heart following cardiac ischemia.

10. The method as claimed in claim 1 wherein the compound is used for the treatment of microinfarcts.

11. The method as claimed in claim 1 wherein the compound is used for the treatment in cases of revascularization of critically narrowed coronary arteries.

12. The method as claimed in claim 1 wherein the compound is used for the treatment of acute myocardial infarction and of damage during and after medical or mechanical lysis thereof.

13. The method as claimed in claim 1 wherein the compound is used for the treatment of sepsis or septic shock.

14. The method as claimed in claim 1 wherein the compound is used for the treatment of diabetes mellitus.

15. The method as claimed in claim 1 wherein the compound inhibits PARP2 at least 5 times more strongly than PARP1.

16. The method as claimed in claim 8 wherein the compound is used for the treatment of generalized epileptic seizures.

17. The method as claimed in claim 16 wherein the compound is used for the treatment of petit mal or tonoclonic seizures.

18. The method as claimed in claim 8 wherein the compound is used for the treatment of partial epileptic seizures.

19. The method as claimed in claim 18 wherein the compound is used for the treatment of temporal lobe or complex partial seizures.

* * * * *